US009645066B1

(12) United States Patent
Yu et al.

(10) Patent No.: US 9,645,066 B1
(45) Date of Patent: May 9, 2017

(54) POLYMER COMPOSITIONS HAVING IMPROVED PROCESSABILITY AND METHODS OF MAKING AND USING SAME

(71) Applicant: Chevron Phillips Chemical Company LP, The Woodlands, TX (US)

(72) Inventors: Youlu Yu, Bartlesville, OK (US); Qing Yang, Bartlesville, OK (US); Paul J. Deslauriers, Owasso, OK (US); Mark J. Lamborn, Bartlesville, OK (US); Yongwoo Inn, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 14/960,047

(22) Filed: Dec. 4, 2015

(51) Int. Cl.
*G01N 11/04* (2006.01)
*G01N 5/00* (2006.01)
*C08F 110/02* (2006.01)
*B29B 13/10* (2006.01)

(52) U.S. Cl.
CPC ............ *G01N 11/04* (2013.01); *C08F 110/02* (2013.01); *G01N 5/00* (2013.01)

(58) Field of Classification Search
CPC .. B29B 13/10; C08F 2500/05; C08F 2500/17; C08F 110/02; G01N 11/04
USPC .......................................... 264/40.1; 209/235
See application file for complete search history.

(56) References Cited

U.S. PATENT DOCUMENTS

| | | |
|---|---|---|
| 3,248,179 A | 4/1966 | Norwood |
| 4,461,873 A * | 7/1984 | Bailey ..................... C08L 23/06 525/240 |
| 4,501,885 A | 2/1985 | Sherk et al. |
| 4,540,538 A | 9/1985 | Corwin et al. |
| 4,588,790 A | 5/1986 | Jenkins, III et al. |
| 4,939,217 A | 7/1990 | Stricklen |
| 5,191,132 A | 3/1993 | Patsidis et al. |
| 5,210,352 A | 5/1993 | Alt et al. |
| 5,347,026 A | 9/1994 | Patsidis et al. |
| 5,352,749 A | 10/1994 | DeChellis et al. |
| 5,399,636 A | 3/1995 | Alt et al. |
| 5,401,817 A | 3/1995 | Palackal et al. |
| 5,409,646 A | 4/1995 | Menon et al. |
| 5,420,320 A | 5/1995 | Zenk et al. |
| 5,436,304 A | 7/1995 | Griffin et al. |
| 5,436,305 A | 7/1995 | Alt et al. |
| 5,451,649 A | 9/1995 | Zenk et al. |
| 5,455,314 A | 10/1995 | Burns et al. |
| 5,496,781 A | 3/1996 | Geerts et al. |
| 5,498,581 A | 3/1996 | Welch et al. |
| 5,541,272 A | 7/1996 | Schmid et al. |
| 5,554,795 A | 9/1996 | Frey et al. |
| 5,563,284 A | 10/1996 | Frey et al. |
| 5,565,175 A | 10/1996 | Hottovy et al. |
| 5,565,592 A | 10/1996 | Patsidis et al. |
| 5,571,880 A | 11/1996 | Alt et al. |
| 5,575,979 A | 11/1996 | Hanson |
| 5,594,078 A | 1/1997 | Welch et al. |
| 5,631,203 A | 5/1997 | Welch et al. |
| 5,631,335 A | 5/1997 | Alt et al. |
| 5,654,454 A | 8/1997 | Peifer et al. |
| 5,668,230 A | 9/1997 | Schertl et al. |
| 5,705,478 A | 1/1998 | Boime |
| 5,705,579 A | 1/1998 | Hawley et al. |
| 6,031,027 A | 2/2000 | Syre et al. |
| 6,114,486 A | 9/2000 | Rowland et al. |
| 6,187,880 B1 | 2/2001 | Welch et al. |
| 6,239,235 B1 | 5/2001 | Hottovy et al. |
| 6,262,191 B1 | 7/2001 | Hottovy et al. |
| 6,299,342 B2 | 10/2001 | Eggen et al. |
| 6,416,663 B1 | 7/2002 | Miroslav et al. |
| 6,509,427 B1 | 1/2003 | Welch et al. |
| 6,573,343 B1 | 6/2003 | Follestad |
| 6,833,415 B2 | 12/2004 | Kendrick et al. |
| 6,855,654 B2 | 2/2005 | Kissin et al. |
| 6,878,454 B1 | 4/2005 | Shannon et al. |
| 6,900,266 B2 | 5/2005 | Raty |
| 7,026,494 B1 | 4/2006 | Yang et al. |
| 8,188,170 B2 | 5/2012 | Zahalka et al. |
| 8,445,599 B2 | 5/2013 | Gustafsson et al. |
| 2005/0127559 A1 | 6/2005 | Eggen et al. |
| 2005/0127599 A1 | 6/2005 | Hopper |
| 2009/0252910 A1 | 10/2009 | Baeckman et al. |
| 2010/0190926 A1 | 7/2010 | Krishnaswamy et al. |
| 2012/0059134 A1 | 3/2012 | Yang et al. |
| 2012/0205832 A1 | 8/2012 | Rahim et al. |
| 2013/0096266 A1* | 4/2013 | Van Dun ................ C08F 10/02 526/65 |
| 2013/0099424 A1 | 4/2013 | Rohatgi et al. |
| 2013/0338314 A1 | 12/2013 | Dewachter et al. |

FOREIGN PATENT DOCUMENTS

| | | |
|---|---|---|
| CN | 103217360 A | 7/2013 |
| NO | 9511264 A1 | 4/1995 |
| WO | 2013037498 A1 | 3/2013 |

OTHER PUBLICATIONS

Alt, Helmut G., et al., "C1-Bridged fluorenylidene cyclopentadienylidene complexes of the type (C13H8-CR1R2-C5H3R)ZrCl2 (R1, R2 = alkyl, phenyl, alkenyl; R = H, alkyl, alkenyl, substituted silyl) as catalyst precursors for the polymerization of ethylene and propylene," Journal of Organometallic Chemistry, 1998, pp. 87-112, vol. 568, Elsevier Science S.A.

(Continued)

*Primary Examiner* — Fred M Teskin
(74) *Attorney, Agent, or Firm* — Conley Rose, P.C.; Rodney B. Carroll; Chad Walter

(57) ABSTRACT

A method of preparing a polymer article comprising determining a zero-shear viscosity for a polymer sample; sieving the polymer sample to produce a plurality of sieved polymer samples; determining a molecular weight distribution for each of the plurality of sieved polymer samples; determining a zero-shear viscosity for each of the plurality of sieved polymer samples; determining a compositional diversity of each of the plurality of sieved polymer samples based on a ratio of the zero shear viscosity for each of the plurality of sieved polymer samples to the zero shear viscosity for the polymer sample; identifying a polymer sample having a ratio of the zero shear viscosity to zero shear viscosity for the polymer sample of from about 0.5 to equal to or greater than about 3; and preparing a polymer article from the identified polymer sample.

20 Claims, 5 Drawing Sheets

(56) References Cited

OTHER PUBLICATIONS

Alt, Helmut G., et al., "C1-verbrückte Fluorenyliden—Indenylidenkomplexe des Typs (C13H8-CR2-C9H6_nR'n)ZrCl2 (n = 0, 1; R = Me, Ph, Butenyl; R' = Alkyl, Alkenyl) als Metallocenkatalysatorvorstufen für die Ethylenpolymerisation," Journal of Organometallic Chemistry, 1998, pp. 153-181, vol. 562, Elsevier Science S.A.

Cardin, D. J., et al., "Chemistry of Organo-Zirconium and -Hafnium Compounds," 1986, 5 pages of cover, publishing information, and contents, Halstead Press: a division of John Wiley & Sons, New York.

Filing receipt and specification for patent application entitled "Polymer Compositions Having Improved Processability and Methods of Making and Using Same," by Paul J. DesLauriers, et al., filed Dec. 4, 2015 as U.S. Appl. No. 14/960,056.

Kajigaeshi, Shoji, et al., "Selective Preparation of Fluorene Derivatives Using the t-Butyl Function as a Positional Protective Group," Bull. Chem. Soc. Jpn., Jan. 1986, pp. 97-103, vol. 59, No. 1, The Chemical Society of Japan.

Köppl, Alexander, et al., "Heterogeneous metallocene catalysts for ethlene polymerization," Journal of Molecular Catalysis A: Chemical, 2001, pp. 23-32, vol. 165, Elsevier Science B.V.

Rauwendaal, Chris, "What's Causing Your Gels?" Plastics Technology, http://www.ptonline.com/articles/what's-causing-your-gels, Mar. 2002, 4 pages, Gardner Business Media, Inc.

Wailes, P. C., et al., "Organometallic Chemistry of Titanium, Zirconium, and Hafnium," 1974, 6 pages of cover, publishing information, and contents, Academic Press, New York.

Office Action dated Sep. 6, 2016 (14 pages), U.S. Appl. No. 14/960,056, filed Dec. 4, 2015.

Foreign communication from a related counterpart application—International Search Report, PCT/US2016/064321, Mar. 2, 2017, 4 pages.

Foreign communication from a related counterpart application—International Search Report, PCT/US2016/063986, Mar. 7, 2017, 5 pages.

\* cited by examiner

POLYMER COMPOSITIONS HAVING IMPROVED PROCESSABILITY AND METHODS OF MAKING AND USING SAME

TECHNICAL FIELD

The present disclosure relates to polymer compositions having improved processability. More particularly, the present disclosure relates to the preparation of polymer articles having reduced defects.

BACKGROUND

Polyolefins are plastic materials useful for making a wide variety of valued products due to their combination of features such as stiffness, ductility, barrier properties, temperature resistance, optical properties, availability, and low cost. In particular, polyethylene (PE) is one of the largest volume polymers consumed in the world. It is a versatile polymer that offers high performance relative to other polymers and alternative materials such as glass or metal. One of the most valued polyolefin products is plastic film. An ongoing need exists for improved polymer compositions displaying desired processing characteristics for producing articles such as film.

SUMMARY

Disclosed herein is a method of preparing a polymer article comprising determining a zero-shear viscosity for a polymer sample; sieving the polymer sample to produce a plurality of sieved polymer samples; determining a molecular weight distribution for each of the plurality of sieved polymer samples; determining a zero-shear viscosity for each of the plurality of sieved polymer samples; determining a compositional diversity of each of the plurality of sieved polymer samples based on a ratio of the zero shear viscosity for each of the plurality of sieved polymer samples to the zero shear viscosity for the polymer sample; identifying a polymer sample having a compositional diversity for the polymer sample of less than about 2; and preparing a polymer article from the identified polymer sample.

Also disclosed herein is a method of preparing a polymer article comprising preparing a polymer sample having a lower molecular weight (LMW) component and a higher molecular weight (HMW) component; sieving the polymer sample to produce a plurality of sieved polymer samples; determining the compositional diversity of each of the plurality of sieved polymer samples based on a molecular weight distribution of each of the plurality of sieved polymer samples; predicting a gel count of an article fabricated from each of the plurality of sieved polymer samples based on the compositional diversity; and fabricating the article from a sieved polymer sample having a predicted gel count of less than about 100 gels/ft².

Also disclosed herein is a method comprising determining a zero-shear viscosity for a sample of a bimodal polymer; sieving the polymer sample to produce a plurality of sieved polymer samples; determining a molecular weight distribution for each of the plurality of sieved polymer samples; determining a zero-shear viscosity for each of the plurality of sieved polymer samples; determining a compositional diversity of each of the plurality of sieved polymer samples based on a ratio of the zero shear viscosity for each of the plurality of sieved polymer samples to the zero shear viscosity for the polymer sample; and predicting a gel count for an article comprising the bimodal polymer.

DETAILED DESCRIPTION

Figure 1:
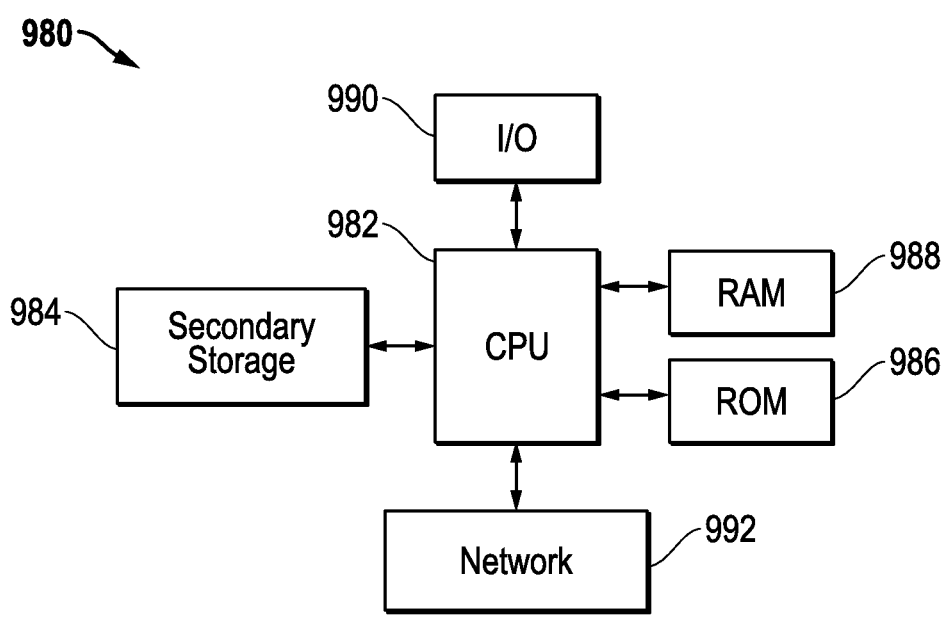
FIG. 1 is a schematic embodiment of a computer system of the type disclosed herein.

Disclosed herein are polymer compositions having improved processability and methods of identifying, making, and using same. Herein a metric of improved processability is the extent of gel formation in a polymer article, for example polymer film. Herein gels refer to visual defects that result due to the presence of discrete bodies that are not sufficiently interspersed with the bulk material and reflect and transmit light differently from the rest of the material. As utilized herein, gels are further defined as particles greater than 200 micron in size. Gels may be formed during the polymerization process and in such cases are termed P-gels. Alternatively the gels may form during extrusion of the polymer and in such cases are termed E-gels. Disclosed herein are methodologies for determining the propensity of polymer compositions to form gels when fabricated into an article.

In an embodiment, a method of the present disclosure comprises preparing a polymer composition. In an embodiment, a polymer composition of the type described herein may be prepared by any suitable methodology, for example by employing one or more catalyst systems, in one or more reactors, in solution, in slurry, or in the gas phase, and/or by varying the monomer concentration in the polymerization reaction, and/or by changing any/all of the materials or parameters involved in the production of the polymer compositions, as will be described in more detail later herein.

The polymer composition of the present disclosure can be produced using various types of polymerization reactors. As used herein, "polymerization reactor" includes any reactor capable of polymerizing olefin monomers to produce homopolymers and/or copolymers. Homopolymers and/or copolymers produced in the reactor may be referred to as resin and/or polymers. The various types of reactors include, but are not limited to those that may be referred to as batch, slurry, gas-phase, solution, high pressure, tubular, autoclave, or other reactor and/or reactors. Gas phase reactors may comprise fluidized bed reactors or staged horizontal reactors. Slurry reactors may comprise vertical and/or horizontal loops. High pressure reactors may comprise autoclave and/or tubular reactors. Reactor types may include batch and/or continuous processes. Continuous processes may use intermittent and/or continuous product discharge or transfer. Processes may also include partial or full direct recycle of un-reacted monomer, un-reacted comonomer, catalyst and/or or co-catalysts, diluents, and/or other materials of the polymerization process.

Polymerization reactor systems of the present disclosure may comprise one type of reactor in a system or multiple reactors of the same or different type, operated in any suitable configuration. Production of polymers in multiple reactors may include several stages in at least two separate polymerization reactors interconnected by a transfer system making it possible to transfer the polymers resulting from the first polymerization reactor into the second reactor. Alternatively, polymerization in multiple reactors may include the transfer, either manual or automatic, of polymer from one reactor to subsequent reactor or reactors for additional polymerization. Alternatively, multi-stage or multi-step polymerization may take place in a single reactor, wherein the conditions are changed such that a different polymerization reaction takes place.

The desired polymerization conditions in one of the reactors may be the same as or different from the operating conditions of any other reactors involved in the overall process of producing the polymer of the present disclosure. Multiple reactor systems may include any combination including, but not limited to multiple loop reactors, multiple gas phase reactors, a combination of loop and gas phase reactors, multiple high pressure reactors or a combination of high pressure with loop and/or gas reactors. The multiple reactors may be operated in series or in parallel. In an embodiment, any arrangement and/or any combination of reactors may be employed to produce the polymer of the present disclosure.

According to one embodiment, the polymerization reactor system may comprise at least one loop slurry reactor. Such reactors may comprise vertical or horizontal loops. Monomer, diluent, catalyst system, and optionally any comonomer may be continuously fed to a loop slurry reactor, where polymerization occurs. Generally, continuous processes may comprise the continuous introduction of a monomer, a catalyst, and/or a diluent into a polymerization reactor and the continuous removal from this reactor of a suspension comprising polymer particles and the diluent. Reactor effluent may be flashed to remove the liquids that comprise the diluent from the solid polymer, monomer and/or comonomer. Various technologies may be used for this separation step including but not limited to, flashing that may include any combination of heat addition and pressure reduction; separation by cyclonic action in either a cyclone or hydrocyclone; separation by centrifugation; or other appropriate method of separation.

Typical slurry polymerization processes (also known as particle-form processes) are disclosed in U.S. Pat. Nos. 3,248,179, 4,501,885, 5,565,175, 5,575,979, 6,239,235, 6,262,191 and 6,833,415, for example; each of which are herein incorporated by reference in their entirety.

Suitable diluents used in slurry polymerization include, but are not limited to, the monomer being polymerized and hydrocarbons that are liquids under reaction conditions. Examples of suitable diluents include, but are not limited to, hydrocarbons such as propane, cyclohexane, isobutane, n-butane, n-pentane, isopentane, neopentane, and n-hexane. Some loop polymerization reactions can occur under bulk conditions where no diluent is used. An example is polymerization of propylene monomer as disclosed in U.S. Pat. No. 5,455,314, which is incorporated by reference herein in its entirety.

According to yet another embodiment, the polymerization reactor may comprise at least one gas phase reactor. Such systems may employ a continuous recycle stream containing one or more monomers continuously cycled through a fluidized bed in the presence of the catalyst under polymerization conditions. A recycle stream may be withdrawn from the fluidized bed and recycled back into the reactor. Simultaneously, polymer product may be withdrawn from the reactor and new or fresh monomer may be added to replace the polymerized monomer. Such gas phase reactors may comprise a process for multi-step gas-phase polymerization of olefins, in which olefins are polymerized in the gaseous phase in at least two independent gas-phase polymerization zones while feeding a catalyst-containing polymer formed in a first polymerization zone to a second polymerization zone. One type of gas phase reactor is disclosed in U.S. Pat. Nos. 4,588,790, 5,352,749, and 5,436,304, each of which is incorporated by reference in its entirety herein.

According to still another embodiment, a high pressure polymerization reactor may comprise a tubular reactor or an autoclave reactor. Tubular reactors may have several zones where fresh monomer, initiators, or catalysts are added. Monomer may be entrained in an inert gaseous stream and introduced at one zone of the reactor. Initiators, catalysts, and/or catalyst components may be entrained in a gaseous stream and introduced at another zone of the reactor. The gas streams may be intermixed for polymerization. Heat and pressure may be employed appropriately to obtain optimal polymerization reaction conditions.

According to yet another embodiment, the polymerization reactor may comprise a solution polymerization reactor wherein the monomer is contacted with the catalyst composition by suitable stirring or other means. A carrier comprising an organic diluent or excess monomer may be employed. If desired, the monomer may be brought in the vapor phase into contact with the catalytic reaction product, in the presence or absence of liquid material. The polymerization zone is maintained at temperatures and pressures that will result in the formation of a solution of the polymer in a reaction medium. Agitation may be employed to obtain better temperature control and to maintain uniform polymerization mixtures throughout the polymerization zone. Adequate means are utilized for dissipating the exothermic heat of polymerization.

Polymerization reactors suitable for the present disclosure may further comprise any combination of at least one raw material feed system, at least one feed system for catalyst or catalyst components, and/or at least one polymer recovery system. Suitable reactor systems for the present disclosure may further comprise systems for feedstock purification, catalyst storage and preparation, extrusion, reactor cooling, polymer recovery, fractionation, recycle, storage, loadout, laboratory analysis, and process control.

Conditions that are controlled for polymerization efficiency and to provide polymer properties include, but are not limited to temperature, pressure, type and quantity of catalyst or co-catalyst, and the concentrations of various reactants. Polymerization temperature can affect catalyst productivity, polymer molecular weight and molecular weight distribution. Suitable polymerization temperatures may be any temperature below the de-polymerization temperature, according to the Gibbs Free Energy Equation. Typically, this includes from about 60° C. to about 280° C., for example, and/or from about 70° C. to about 110° C., depending upon the type of polymerization reactor and/or polymerization process.

Suitable pressures will also vary according to the reactor and polymerization process. The pressure for liquid phase polymerization in a loop reactor is typically less than 1000 psig. Pressure for gas phase polymerization is usually at about 200-500 psig. High pressure polymerization in tubular or autoclave reactors is generally run at about 20,000 to 75,000 psig. Polymerization reactors can also be operated in a supercritical region occurring at generally higher temperatures and pressures. Operation above the critical point of a pressure/temperature diagram (supercritical phase) may offer advantages.

The concentration of various reactants can be controlled to produce polymers with certain physical and mechanical properties. The proposed end-use product that will be formed by the polymer and the method of forming that product may be varied to determine the desired final product properties. Mechanical properties include, but are not limited to tensile strength, flexural modulus, impact resistance, creep, stress relaxation and hardness tests. Physical properties include, but are not limited to density, molecular weight, molecular weight distribution, melting temperature, glass transition temperature, temperature melt of crystallization, density, stereoregularity, crack growth, short chain branching, long chain branching and rheological measurements.

The concentrations of monomer, co-monomer, hydrogen, co-catalyst, modifiers, and electron donors are generally important in producing specific polymer properties. Comonomer may be used to control product density. Hydrogen may be used to control product molecular weight. Co-catalysts may be used to alkylate, scavenge poisons and/or control molecular weight. The concentration of poisons may be minimized, as poisons may impact the reactions and/or otherwise affect polymer product properties. Modifiers may be used to control product properties and electron donors may affect stereoregularity.

In an embodiment, a method of preparing a polymer composition comprises contacting an olefin monomer (e.g., ethylene) with a catalyst system under conditions suitable for the formation of a polymer of the type described herein. In an embodiment, the catalyst system comprises a transition-metal complex. The terms "catalyst composition," "catalyst mixture," "catalyst system," and the like, do not depend upon the actual product resulting from the contact or reaction of the components of the mixtures, the nature of the active catalytic site, or the fate of the co-catalyst, the catalyst, any olefin monomer used to prepare a precontacted mixture, or the activator-support, after combining these components. Therefore, the terms "catalyst composition," "catalyst mixture," "catalyst system," and the like, can include both heterogeneous compositions and homogenous compositions.

In an embodiment, a catalyst system suitable for the preparation of a polymer composition comprises at least one metallocene-containing compound. Herein, the term "metallocene" describes a compound comprising at least one $\eta^3$ to $\eta^5$-cycloalkadienyl-type moiety, wherein $\eta^3$ to $\eta^5$-cycloalkadienyl moieties include cyclopentadienyl ligands, indenyl ligands, fluorenyl ligands, and the like, including partially saturated or substituted derivatives or analogs of any of these. Possible substituents on these ligands include hydrogen, therefore the description "substituted derivatives thereof" in this disclosure comprises partially saturated ligands such as tetrahydroindenyl, tetrahydrofluorenyl, octahydrofluorenyl, partially saturated indenyl, partially saturated fluorenyl, substituted partially saturated indenyl, substituted partially saturated fluorenyl, and the like.

In an embodiment, a catalyst system suitable for the preparation of a polymer composition comprises at least two metallocene-containing compounds. Nonlimiting examples of metallocene-containing compounds suitable for use in this disclosure are described in more detail in U.S. Pat. Nos. 4,939,217; 5,191,132; 5,210,352; 5,347,026; 5,399,636; 5,401,817; 5,420,320; 5,436,305; 5,451,649; 5,496,781; 5,498,581; 5,541,272; 5,554,795; 5,563,284; 5,565,592; 5,571,880; 5,594,078; 5,631,203; 5,631,335; 5,654,454; 5,668,230; 5,705,478; 5,705,579; 6,187,880; 6,509,427; 7,026,494, and U.S. Patent App. Nos. 20100190926 A1 and 20120059134, each of which is incorporated by reference herein in its entirety. Other processes to prepare metallocene compounds suitable for use in this disclosure have been reported in references such as: Koppl, A. Alt, H. G. J. Mol. Catal. A. 2001, 165, 23; Kajigaeshi, S.; Kadowaki, T.; Nishida, A.; Fujisaki, S. The Chemical Society of Japan, 1986, 59, 97; Alt, H. G.; Jung, M.; Kehr, G. J. Organomet. Chem. 1998, 562, 153-181; and Alt, H. G.; Jung, M. J. Organomet. Chem. 1998, 568, 87-112; each of which is incorporated by reference herein in its entirety. The following treatises also describe such methods: Wailes, P. C.; Coutts, R. S. P.; Weigold, H. in Organometallic Chemistry of Titanium, Zirconium, and Hafnium, Academic; New York, 1974; Cardin, D. J.; Lappert, M. F.; and Raston, C. L.; Chemistry of Organo-Zirconium and -Hafnium Compounds; Halstead Press; New York, 1986. In an embodiment, the polymer composition is prepared using a catalyst system comprising two metallocene-containing compounds and may be characterized as a dual metallocene polymer or a dual metallocene resin. In an embodiment such dual-metallocene catalysts may be used to prepare resins of the type disclosed herein.

In an embodiment, the dual metallocene catalyst used for preparation of the polymer composition comprises an unbridged metallocene, designated MTE-A. In an embodiment, MTE-A is a compound that may be characterized by one of general formulas 1 or 2:

Formula 1

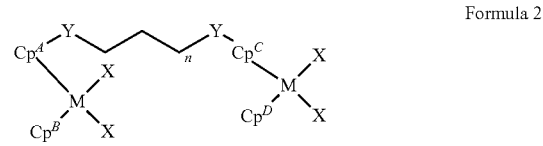

Formula 2 where each X is independently F, Cl, Br, I, methyl, benzyl, phenyl, H, $BH_4$, a hydrocarbyloxide group having up to 20 carbon atoms, a hydrocarbylamino group having up to 20 carbon atoms, a trihydrocarbylsilyl group having up to 20 carbon atoms, $OBR'_2$ wherein R' may be an alkyl group having up to 12 carbon atoms or an aryl group having up to 12 carbon atoms, and $SO_3R''$, wherein R'' may be an alkyl group having up to 12 carbon atoms or an aryl group having up to 12 carbon atoms; Y is a $CR_2$ or $SiR_2$ group where R is hydrogen or a hydrocarbyl group; $Cp^A$, $Cp^B$, $Cp^C$, and $Cp^D$ are each independently a substituted or unsubstituted cyclopentadienyl group, or indenyl group, and where any substituent on $Cp^A$, $Cp^B$, $Cp^C$, and $Cp^D$ can be H, a hydrocarbyl group having up to 18 carbon atoms or a hydrocarbylsilyl group having up to 18 carbon atoms. In an embodiment, MTE-A is a dinuclear compound wherein each metal moiety has the same structural characteristic described previously herein.

In an embodiment, the dual metallocene catalyst used for preparation of the polymer composition further comprises a bridged metallocene compound hereinafter designated MTE-B. In an embodiment, MTE-B can be characterized by one of general formulas 3 or 4:

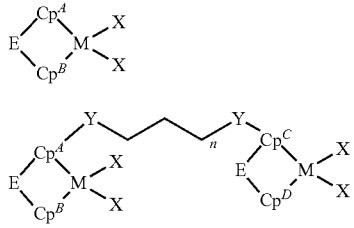

Formula 3

Formula 4 where M is Ti, Zr or Hf; each X is independently F, Cl, Br, I, methyl, phenyl, benzyl, H, $BH_4$, a hydrocarbyloxide group having up to 20 carbon atoms, a hydrocarbylamino group having up to 20 carbon atoms, a trihydrocarbylsilyl group having up to 20 carbon atoms, $OBR'_2$ wherein R' may be an alkyl group having up to 12 carbon atoms or an aryl group having up to 12 carbon atoms, or $SO_3R''$ wherein R'' may be an alkyl group having up to 12 carbon atoms or an aryl group having up to 12 carbon atoms; Y is a $CR_2$, $SiR_2$, or $R_2CCR_2$ group which may be linear or cyclic and where R is hydrogen or a hydrocarbyl group; $Cp^A$, $Cp^B$, $Cp^C$, and $Cp^D$ are each independently a substituted or unsubstituted cyclopentadienyl group, indenyl group, or flourenyl group and where any substituent on $Cp^A$, $Cp^B$, $Cp^C$, and $Cp^D$ can be H, a hydrocarbyl group having up to 18 carbon atoms or a hydrocarbylsilyl group having up to 18 carbon atoms. E represents a bridging group which may comprise (i) a cyclic or heterocyclic moiety having up to 18 carbon atoms, (ii) a group represented by the general formula $E^A R^{3A} R^{4A}$, wherein $E^A$ is C, Si, Ge, or B, and $R^{3A}$ and $R^{4A}$ are independently H or a hydrocarbyl group having up to 18 carbon atoms, (iii) a group represented by the general formula $-CR^{3B}R^{4B}-CR^{3C}R^{4C}-$, wherein $R^{3B}$, $R^{4B}$, $R^{3C}$, and $R^{4C}$ are independently H or a hydrocarbyl group having up to 10 carbon atoms, or (iv) a group represented by the general formula $SiR_2-CR_2$ where X is Si or C and R is a hydrogen or hydrocarbyl group; or $-SiR^{3D}R^{4D}-SiR^{3E}R^{4E}-$, wherein $R^{3D}$, $R^{4D}$, $R^{3E}$, and $R^{4E}$ are independently H or a hydrocarbyl group having up to 10 carbon atoms, and wherein at least one of $R^{3A}$, $R^{3B}$, $R^{4A}$, $R^{4B}$, $R^{3C}$, $R^{4C}$, $R^{3D}$, $R^{4D}$, $R^{3E}$, $R^{4E}$, or the substituent on Cp, $Cp_1$, or $Cp_2$, is (1) a terminal alkenyl group having up to 12 carbon atoms or (2) a dinuclear compound wherein each metal moiety has the same structural characteristic as MTE-B.

The polymer composition may comprise additives. Examples of additives include, but are not limited to, antistatic agents, colorants, stabilizers, nucleators, surface modifiers, pigments, slip agents, antiblocks, tackifiers, polymer processing aids, and combinations thereof. Such additives may be used singularly or in combination and may be contacted with the polymer before, during, or after preparation of the polymer composition as described herein. Such additives may be added via any suitable technique, for example during an extrusion or compounding step such as during pelletization or subsequent processing into an end use article.

In an embodiment, the polymer composition comprises polyethylene. For example the polymer composition may comprise a polyethylene homopolymer. It is to be understood that an inconsequential amount of comonomer may be present in the polymers disclosed herein and the polymer still be considered a homopolymer. Herein an inconsequential amount of a comonomer refers to an amount that does not substantively affect the properties of the polymer disclosed herein. For example a comonomer can be present in an amount of less than about 0.5 wt. %, 0.1 wt. %, or 0.01 wt. % based on the total weight of polymer.

In an alternative embodiment, the polymer composition comprises a polyethylene copolymer. Examples of suitable comonomers include without limitation unsaturated hydrocarbons having from 3 to 20 carbon atoms such as propylene, 1-butene, 1-pentene, 1-hexene, 3-methyl-1-butene, 4-methyl-1-pentene, 1-heptene, 1-octene, 1-nonene, 1-decene, and mixtures thereof. In some embodiments the polymer composition is copolymer of ethylene and 1-hexene. The applicability of the aspects and features disclosed herein to linear olefin polymers other than ethylene (e.g., propylene and 1-butylene) and olefin copolymers are also contemplated.

In an embodiment, a polymer composition of the type described herein (e.g., PE) comprises a polymer blend, e.g., a blend of two or more component polymers. For example, the polymer composition may be a physical or mechanical blend of polymers, alternatively the polymer composition may be a reactor blend of polymers. In an embodiment, a process for the preparation of a polymer composition of the type disclosed herein comprises the preparation of each component of the polymer composition independent of the other components. The process may comprise polymerization of an alpha-olefin monomer in the presence of a catalyst system under a first set of reaction conditions to form a first component of the polymer composition. The process may further comprise polymerization of an alpha-olefin in the presence of a catalyst system under a second set of reaction conditions to form a second component of the polymer composition. The formation of the second component may be carried out in the presence of the first component (e.g., a reactor blend) or in the absence of the first component (and the two components subsequently blended, for example via mechanical blending, co-extrusion, etc.). A process for preparation of a polymer composition may further comprise contacting the first and second components utilizing any appropriate methodology (e.g., mechanical mixing). In such an embodiment, the resultant polymer composition comprises a physical blend of the first and second component.

Alternatively, a process for the preparation of a polymer composition of the type disclosed herein comprises polymerization of an alpha-olefin monomer in the presence of at least two different catalytic materials or catalysts, for example a catalyst system comprising at least two transition metal complexes. For example, the catalyst system may comprise a first and a second transition metal complex wherein the first and second transition metal complexes are different. In an embodiment, the catalyst system comprises at least two metallocene complexes and results in the simultaneous formation of at least two components of the polymer composition when both catalysts are employed in a single reactor. In the alternative, a first catalyst system comprising a first metallocene complex is associated with a first reactor. Alpha-olefin monomer may be contacted with the first catalyst system in the first reactor and conditions adjusted such that polymerization of the alpha-olefin monomer and a first component of the polymer composition is produced. The first component may then be contacted with a second catalyst system and alpha-olefin monomer under conditions to result in the polymerization of the alpha-olefin monomer and formation of the second component of the polymer composition. In such an embodiment, the components of the polymer composition are produced sequentially.

In the aforementioned embodiments employing at least two metallocene complexes, the polymer composition formed may be described as a reactor blend of the two components.

A polymer composition of the type described herein may be a multimodal resin. Herein, the "modality" of a polymer resin refers to the form of its molecular weight distribution curve, i.e., the appearance of the graph of the polymer weight fraction as a function of its molecular weight, as may be displayed by, for example, gel permeation chromatography (GPC). The polymer weight fraction refers to the weight fraction of molecules of a given size. A polymer having a molecular weight distribution curve showing a single peak may be referred to as a unimodal polymer, a polymer having a curve showing two distinct peaks may be referred to as bimodal or a bimodal-like polymer, a polymer having a curve showing three distinct peaks may be referred to as trimodal polymer, etc. Polymers having molecular weight distribution curves showing more than one peak may be collectively referred to as multimodal polymers or resins. It is acknowledged that, in some instances, a multimodal polymer may appear to have a single peak via, for example, GPC analysis, when in fact the polymer itself is multimodal. In such instances, overlap of peaks may obscure the presence of other peaks and may imply unimodality, when in fact multimodality is a more accurate representation of the nature of the polymer or polymers.

In an embodiment, the polymer composition is characterized as a bimodal resin. A GPC of a polymer composition of the type described herein may display the following identifiable features (i) a peak attributable to a higher molecular weight (HMW) component and (ii) a peak attributable to a lower molecular weight (LMW) component. It is to be understood that a LMW component corresponds to a subpopulation of the polymer composition which on a GPC profile will show a Gaussian-like distribution of molecular weights centered around some peak maximum value or range that has a lesser numerical value than the HMW component which is another subpopulation of the polymer composition also characterized by a Gaussian-like distribution with a peak maximum value or range. In an embodiment, a GPC plot of the polymer composition exhibits a LMW component that is baseline separated from the HMW component. In an alternative embodiment, a GPC plot of the polymer composition exhibits a LMW component that is not baseline separated from the HMW component. In such embodiments, the GPC plot may be deconvoluted using any suitable methodology to extract the independent GPC profiles of the LMW and HMW components.

In an embodiment, the HMW component is present in a weight percentage based on the total weight of the polymer composition of from about 30% to about 70%, alternatively from about 35% to about 60%, or alternatively from about 35% to about 65%, or alternatively from about 40% to about 55% with the remainder of the composition primarily being the LMW component.

The LMW component may be characterized by a weight average molecular weight ($M_w$) of from about 10 kg/mol to about 200 kg/mol, alternatively from about 25 kg/mol to about 200 kg/mol, or alternatively from about 100 kg/mol to about 200 kg/mol. The HMW component may be characterized by a $M_w$ of from about 300 kg/mol to about 1000 kg/mol, alternatively from about 350 kg/mol to about 1000 kg/mol, or alternatively from about 650 kg/mol to about 1000 kg/mol. The $M_w$ describes the molecular weight distribution of the polymer composition and is calculated according to equation 1:

$$M_w = \frac{\sum_i N_i M_i^2}{\sum_i N_i M_i} \quad (1)$$

where $N_i$ is the number of molecules of molecular weight $M_i$. As used herein $M_w$ is measured by gel permeation chromatography.

In one or more embodiments, polymer compositions of the type described herein are characterized by a density of from about 0.912 g/cc to about 0.960 g/cc, alternatively from about 0.930 g/cc to about 0.958 g/cc, or alternatively from about 0.940 g/cc to about 0.955 g/cc as determined in accordance with ASTM D1505.

In one or more embodiments, the polymer composition exhibits a melt index (MI) in the range of from about 0.00001 dg/min to about 1 dg/min, alternatively of from about 0.01 dg/min to about 1 dg/min, alternatively from about 0.01 dg/min to about 0.8 dg/min, or alternatively from about 0.05 dg/min to about 0.3 dg/min. The melt index (MI) refers to the amount of a polymer which can be forced through an extrusion rheometer orifice of 0.0825 inch diameter when subjected to a force of 2160 grams in ten minutes at 190° C., as determined in accordance with ASTM D1238.

In an embodiment, a method of the present disclosure comprises determining the compositional diversity of a polymer composition of the type disclosed herein. Herein the compositional diversity is designated Ω. The polymer composition whose diversity is being evaluated may be in the form of fluff where fluff refers to the product formed at the end of the polymerization process and obtained from the polymerization reactor. In an embodiment, the fluff has not undergone any further post-reactor processing that would change the physical form of the polymer (e.g., has not undergone melting, extrusion, pellitization, or the like).

In an embodiment, the compositional diversity of a fluff (i.e., polymer composition as a whole) is determined by calculating the ratio of zero shear viscosity, calculating the standard deviation of the molecular weight distribution, and/or calculating the high frequency viscosity for the fluff and/or subpopulations derived from the fluff. In embodiments where the compositional diversity is calculated utilizing the ratio of zero shear viscosity and/or the standard deviation of the molecular weight distribution; these calculations involve determining a ratio between a metric associated with the fluff (i.e., polymer composition as a whole) and the metric as associated with a subpopulation of the fluff. In such embodiments, subpopulations of the fluff (i.e., polymer composition as a whole) are prepared by sieving.

The method for determining the diversity of the fluff (i.e., polymer composition as a whole) may comprise sieving the fluff into subpopulations on the basis of particle size. As used herein, particle size may be determined in accordance with the ability of a polymer particle to pass through a woven wire test sieve as described in ASTM E11-09. For purposes of this disclosure, all references to a woven wire test sieve refer to a woven wire test sieve as described in ASTM E11-09. As used herein, reference to particle size refers to the size of an aperture (e.g., nominal aperture dimension) through which the polymer particle will pass, and for brevity this is referred to herein as "particle size." An aperture is an opening in a sieve (e.g., woven wire test sieve) or a screen for particles to pass through. The aperture of the woven wire test sieve is a square and the nominal aperture dimension refers to the width of the square aperture. For example, a polymer particle is considered to have a size of less than about 2.00 mm if the polymer particle passes through the aperture of a 10 mesh woven wire test sieve, where the mesh size is given based on U.S. Sieve Series. As will be appreciated by one of skill in the art, and with the help of this disclosure, polymer particles can have a plurality of shapes, such as for example cylindrical, discoidal, spherical, tabular, ellipsoidal, equant, irregular, or combinations thereof. Generally, for a particle to pass through an aperture of a sieve or screen, it is not necessary for all dimensions of the particle to be smaller than the aperture of such screen or sieve, and it could be enough for one of the dimensions of the particle to be smaller than the aperture of such screen or sieve. For example, if a cylindrical shaped particle that has a diameter of 1.00 mm and a length of 2.50 mm passes through the aperture of a 10 mesh woven wire test sieve, where the mesh size is according to U.S. Sieve Series, such particle is considered to have a particle size of less than about 2.00 mm.

In an embodiment, a polymer composition of the type disclosed herein in fluff form is sieved into a plurality of subpopulations based on particle size. The polymer composition may be subjected to at least 3 sieves to produce at least 3 subpopulations, alternatively at least 4 sieves to produce at least 4 subpopulations, or alternatively at least 5 sieves to produce at least 5 subpopulations. In an embodiment, the sieves may have any suitable mesh size, for example the sieves may range in mesh size from about 10 mesh to about 300 mesh, or alternatively from about 20 mesh to about 200 mesh based on the U.S. Sieve Series. Herein each subpopulation is denoted $\delta_x$ where x represents the mesh size of the subpopulation. For example, a polymer composition of the type disclosed herein may be sieved into subpopulations such as $\delta_{10}$, $\delta_{25}$, $\delta_{50}$, and $\delta_{100}$ representing 10 mesh, 25 mesh, 50 mesh and 100 mesh, respectively.

In an embodiment, the gel count of a fluff (i.e., polymer composition as a whole) is predicted based on a univariate analysis of the fluff using a single metric such as the ratio of zero shear viscosity, high frequency viscosity, or standard deviation of the MWD. Each of these properties and methods of determining same are described herein.

In an embodiment, the compositional diversity (n) of the fluff (i.e., polymer composition as a whole) may be evaluated based on a ratio of the zero shear viscosity of one of the sieved polymer samples ($\eta_{0\delta x}$) to the zero shear viscosity of the polymer composition as a whole ($\eta_{0\Sigma}$). The $\eta_{0\delta x}$ for the sieved polymer sample and/or and the $\eta_{0\Sigma}$ for the fluff may be determined using any suitable methodology. For example, zero shear viscosity values may be obtained via the 3.4 power law relationship where the zero shear viscosity is proportional to $M_w^{3.4}$. In an embodiment, $\eta_{0\delta x}$, $\eta_{0\Sigma}$, or both are obtained from the Arnett 3.4-power law (equation 2)

$$\eta_o = kM_w^{3.4} \tag{2}$$

where $\eta_o$=zero shear viscosity (Pa·s) [defines the Newtonian plateau]

k=Arnett law constant $M_w$=weight average molecular weight (Da)

where the molecular weight can be determined by conventional GPC method coupled with broad calibration.

In an embodiment, the zero shear viscosity of the sieved polymer sample ($\eta_{0\delta x}$) is determined for at least one mesh size (i.e., x value) of from about 10 mesh to about 200 mesh, alternatively from about 10 mesh to about 60 mesh, or alternatively from about 10 mesh to about 35 mesh. For example, calculating the ratio of zero shear viscosity may be carried out using the values for $\eta_{0\delta 10}$ and $\eta_{0\Sigma}$ or the zero shear viscosity value for the subpopulation of fluff corresponding to a 10 mesh particle size and the zero shear viscosity value for the fluff (i.e., polymer composition as a whole), respectively. In an embodiment the value for the ratio of $\eta_{0\delta x}/\eta_{0\Sigma}$ is less than about 2, alternatively from about 0.8 to about 1.8, or alternatively from about 0.8 to about 1.2 and such a composition is predicted to have a low gel count where a low gel count refers to equal to or less than about 100 gels/ft². It is contemplated that values for $\eta_{0\delta x}/\eta_{0\Sigma}$ within the disclosed ranges indicate a fluff (i.e., polymer composition as a whole) having a low compositional diversity and concomitantly a reduced tendency to form gels.

In an embodiment, the compositional diversity ($\Omega$) of the fluff (i.e., polymer composition as a whole) may be evaluated based on the difference in the molecular weight distributions (MWD) between the sieved polymer samples. In an embodiment, the fluff (i.e., polymer composition as a whole) is sieved as described previously herein, using 10, 20, 35, 60, 100, and 200 mesh sieves and a pan to capture fluff passing through the 200 mesh sieve. The MWD for each of the sieved and pan fluff samples may be determined and can be denoted MWD$\delta_x$. In an embodiment, $\Omega$ is equal to the sum of standard deviations between the MWD$\delta_x$ determined at 74 equally spaced values of the logarithmic molecular weight (denoted as Log(M)), starting at 2.3 and ending at 6.5, as indicated by equation 3.

$$\Omega = \Sigma_{n=1}^{74}(MWD\delta_x)_n \tag{3}$$

In an embodiment, a fluff (i.e., polymer composition as a whole) has an $\Omega$ ranging from about 0 to about 5, alternatively from about 0 to about 2, alternatively from about 0.7 to about 2.0, or alternatively from about 0.7 to about 1.4 and is characterized as having a low compositional diversity and concomitantly a reduced tendency to form gels. In an embodiment, $\Omega$ is less than about 2.

In an embodiment, the mixing efficiency of the fluff may be evaluated based on the high frequency viscosity of the polymer composition as a whole, $\eta@100$. Herein the $\eta@100$ refers to the viscosity of the fluff (i.e., polymer composition as a whole) at 100 rad/s as determined by small amplitude oscillatory frequency sweep test at 190° C. It is contemplated that (@100) is proportional to mixing efficiency and consequently larger values of $\eta@100$ for the fluff (i.e., polymer composition as a whole) indicate improved mixing efficiency and concomitantly a reduced tendency to form gels. In an embodiment, $\eta@100$ of the fluff (i.e., polymer composition as a whole) ranges from about 1900 Pa·s to about 4500 Pa·s, alternatively from about 2000 Pa·s to about 4200 Pa·s, or alternatively from about 2400 Pa·s to about 4000 Pa·s and such a composition is predicted to have a low gel count where a low gel count refers to equal to or less than about 100 gels/ft².

In some embodiments of this disclosure, a bivariate analysis of the compositional diversity of the fluff (i.e., polymer composition as a whole) is carried out. In such analyses two metrics are analyzed in order to assess the propensity of the fluff (i.e., polymer composition as a whole) to form gels when fabricated into a polymer article.

In an embodiment, the bivariate analysis comprises determining the propensity of the fluff to form gels as a function of both the zero shear viscosity ratio and the amount of HMW component.

The zero shear viscosity may be determined as described previously herein. In such embodiments, fluff having a percentage of HMW component ranging from about 30 wt. % to about 70 wt. % and a ratio of zero shear viscosity ratio ranging from about 0.8 to about 2.5 may be predicted to form articles having a low gel count. Alternatively, fluff having a percentage of HMW component ranging from about 35 wt. % to about 60 wt. % and a zero shear viscosity ratio ranging from about 0.9 to about 2.0 may be predicted to form articles having a low gel count (i.e., equal to or less than about 100 gels/ft$^2$). Alternatively, fluff having a percentage of HMW component ranging from about 40 wt. % to about 55 wt. % and a zero shear viscosity ranging from about 0.8 to about 1.2 may be predicted to form articles having a low gel count.

In an embodiment, the bivariate analysis comprises determining the propensity of a fluff to form gels as a function of both the compositional diversity and the high frequency viscosity of the polymer composition as a whole, $\eta@100$, in accordance with equation 4.

$$800 \times \Omega - \eta@100 + 1300 = \theta \quad (4)$$

where theta ($\theta$) is the propensity to form gels. The propensity of the fluff to form gels is low (i.e., less than 100 gels/ft$^2$) when $\Omega$ is less than 1.4 or when $\theta$ is less than 0.

The compositional diversity ($\Omega$) may be calculated as disclosed herein using properties such as the ratio of zero shear viscosity or standard deviation of the MWD.

It is contemplated that with the aid and benefit of the present disclosure any number of multivariate analysis (i.e., 3 or more parameters) may be considered simultaneously in assessing the compositional diversity of the fluff and further that any suitable methodology (e.g., empirical measurements) may be employed to establish a mathematical relationship between the parameters analyzed and the compositional diversity.

In an embodiment, a fluff of the type disclosed herein is predicted to generate articles having gel counts that are greater than some user and/or process desired range or value (e.g., greater than about 100 gels/ft$^2$). In such embodiments, the polymerization reaction utilized in production of the polymer composition may be adjusted to facilitate the production of a fluff that would have a gel count that is within some user and/or process desired range. For example, the gel count may be adjusted (e.g., reduced) by increasing the HMW content, reducing the fluff diversity, reducing the difference between the weight average molecular weight of the HMW component and the LMW component by either increasing weight average molecular weight of the LMW component or decreasing that of the HMW or both, and/or making uniformly active catalytic species on the catalyst particles.

In some embodiments, adjustments to the polymerization reaction conditions are made on the fly. For example, the polymer composition may have a sample taken under a particular set of polymerization reaction conditions. Prior to the production of an intended quantity of polymer, the gel count of a sample of the fluff may be predicted and the polymerization reaction conditions adjusted to affect the gel count of the remaining amount of polymer to be produced.

In an embodiment, a fluff of the type disclosed herein is predicted to generate articles having gel counts that are greater than some user and/or process desired range or value. In such embodiments, the fluff may be sieved to produce a plurality of subpopulations characterized by the polymer particle size (e.g., $\delta_{25}$). In an embodiment, at least two of the subpopulations having similar MW or MWD values are combined to produce a low compositional diversity polymer composition (LHPC) that is subsequently utilized to fabricate an article. Herein similar MW or MWD values refer to values that differ by from about 1% to about 20%, alternatively from about 5% to about 20%, or alternatively less than about 15%.

In one or more embodiments the fluff produced as disclosed herein may be formed into an article. For example, a fluff may be extruded into an end use article such as a container, a cup, a tray, a pallet, a toy, or a component of another product. In an embodiment, fluff produced as described herein (e.g., polyethylene) may be formed into films which can be useful in food packaging.

In one or more embodiments the fluff produced as disclosed herein may (i.e., LHPC) be formed into films. The films of this disclosure may be produced by any suitable method and under any suitable conditions for the production of films. In an embodiment, the fluff is formed into films through a cast film process. In a cast film process, plastic melt is extruded through a slit die onto a chilled, polished roll to freeze the film. The speed of the roll controls the draw down ratio and film gauge. The film moves forward toward a second wounding roll where cooling is completed.

In another embodiment, the fluff disclosed herein is formed into films through a blown film process. Blown film processes may include forcing molten polymer through a circular die, which is then blown. The resultant bubble is then flattened and cut into strips, that when rolled, produces rolls of flat film.

The films formed from the fluff disclosed herein may be of any thickness desired by the user. Alternatively, the polymer resins of this disclosure may be formed into films having a thickness of from about 0.3 mils (7 microns) to about 3 mils (76 microns), or from about 0.5 mils (12 microns) to about 2 mils (50 microns), or from about 0.8 mil (20 microns) to about 1.6 mils (40 microns).

In an embodiment, films formed from an LHPC of the type disclosed herein are characterized by gels counts of from about 10 gels/ft$^2$ to about 100 gels/ft$^2$, alternatively from about 10 gels/ft$^2$ to about 75 gels/ft$^2$' or alternatively from about 0 gels/ft$^2$ to about 50 gels/ft$^2$.

FIG. 1 illustrates a computer system 980 suitable for implementing one or more embodiments disclosed herein. For example, the results of determining one or more metrics for a fluff (i.e. polymer composition as a whole) and/or one or more subpopulations of the composition (e.g., sieved sample) may be transmitted to a computer system which can then determine one or more parameters (e.g., compositional diversity) and/or indicators of the propensity of a fluff (i.e., polymer composition as a whole) to form gels when fabricated into an article (e.g., film). The computer system 980 includes a processor 982 (which may be referred to as a central processor unit or CPU) that is in communication with memory devices including secondary storage 984, read only memory (ROM) 986, random access memory (RAM) 988, input/output (I/O) devices 990, and network connectivity devices 992. The processor 982 may be implemented as one or more CPU chips.

It is understood that by programming and/or loading executable instructions onto the computer system 980, at least one of the CPU 982, the RAM 988, and the ROM 986 are changed, transforming the computer system 980 in part into a particular machine or apparatus having the novel functionality taught by the present disclosure. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by any suitable design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

The secondary storage 984 is typically comprised of one or more disk drives or tape drives and is used for non-volatile storage of data and as an over-flow data storage device if RAM 988 is not large enough to hold all working data. Secondary storage 984 may be used to store programs which are loaded into RAM 988 when such programs are selected for execution. The ROM 986 is used to store instructions and perhaps data which are read during program execution. ROM 986 is a non-volatile memory device which typically has a small memory capacity relative to the larger memory capacity of secondary storage 984. The RAM 988 is used to store volatile data and perhaps to store instructions. Access to both ROM 986 and RAM 988 is typically faster than to secondary storage 984. The secondary storage 984, the RAM 988, and/or the ROM 986 may be referred to in some contexts as computer readable storage media and/or non-transitory computer readable media.

I/O devices 990 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 992 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. These network connectivity devices 992 may enable the processor 982 to communicate with the Internet or one or more intranets. With such a network connection, it is contemplated that the processor 982 might receive information from the network, or might output information to the network in the course of performing the above-described method steps. Such information, which is often represented as a sequence of instructions to be executed using processor 982, may be received from and outputted to the network, for example, in the form of a computer data signal embodied in a carrier wave.

Such information, which may include data or instructions to be executed using processor 982 for example, may be received from and outputted to the network, for example, in the form of a computer data baseband signal or signal embodied in a carrier wave. The baseband signal or signal embedded in the carrier wave, or other types of signals currently used or hereafter developed, may be generated according to several methods well known to one skilled in the art. The baseband signal and/or signal embedded in the carrier wave may be referred to in some contexts as a transitory signal.

The processor 982 executes instructions, codes, computer programs, scripts which it accesses from hard disk, floppy disk, optical disk (these various disk based systems may all be considered secondary storage 984), ROM 986, RAM 988, or the network connectivity devices 992. While only one processor 982 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 984, for example, hard drives, floppy disks, optical disks, and/or other device, the ROM 986, and/or the RAM 988 may be referred to in some contexts as non-transitory instructions and/or non-transitory information.

In an embodiment, the computer system 980 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computer system 980 to provide the functionality of a number of servers that is not directly bound to the number of computers in the computer system 980. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an embodiment, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 980, at least portions of the contents of the computer program product to the secondary storage 984, to the ROM 986, to the RAM 988, and/or to other non-volatile memory and volatile memory of the computer system 980. The processor 982 may process the executable instructions and/or data structures in part by directly accessing the computer program product, for example by reading from a CD-ROM disk inserted into a disk drive peripheral of the computer system 980. Alternatively, the processor 982 may process the executable instructions and/or data structures by remotely accessing the computer program product, for example by downloading the executable instructions and/or data structures from a remote server through the network connectivity devices 992. The computer program product may comprise instructions that promote the loading and/or copying of data, data structures, files, and/or executable instructions to the secondary storage 984, to the ROM 986, to the RAM 988, and/or to other non-volatile memory and volatile memory of the computer system 980.

In some contexts, the secondary storage 984, the ROM 986, and the RAM 988 may be referred to as a non-transitory computer readable medium or a computer readable storage media. A dynamic RAM embodiment of the RAM 988, likewise, may be referred to as a non-transitory computer readable medium in that while the dynamic RAM receives electrical power and is operated in accordance with its design, for example during a period of time during which the computer 980 is turned on and operational, the dynamic RAM stores information that is written to it. Similarly, the processor 982 may comprise an internal RAM, an internal ROM, a cache memory, and/or other internal non-transitory storage blocks, sections, or components that may be referred to in some contexts as non-transitory computer readable media or computer readable storage media.

In an embodiment, one or more metrics of the type disclosed herein for evaluating the compositional diversity of a fluff (i.e., polymer composition as a whole) are transmitted to a computer system of the type disclosed herein. The computer system may be characterized by software that utilizes the transmitted values to provide information to the user as to the propensity of the fluff (i.e., polymer composition as a whole) to form gels when fabricated into an article (e.g., film).

The actual gel count for any polymer composition disclosed herein may y be determined using any suitable methodology, for example in accordance with ASTM D2765-01 Method A in xylene or by optical measurement or by visual assessment (e.g., counting the number of gels per unit area).

EXAMPLES

For each of the following examples molecular weights and molecular weight distributions were obtained using a PL 220 GPC/SEC high temperature chromatography unit (Polymer Laboratories, now an Agilent Company) with 1,2,4-trichlorobenzene (TCB) as the solvent, with a flow rate of 0.5-2.0 mL/minute at a temperature of 145° C. BHT (2,6-di-tert-butyl-4-methylphenol) at a concentration of 0.5 g/L was used as a stabilizer in the TCB. An injection volume of 100-400 µL was used with a nominal polymer concentration of 0.5-1.5 mg/mL. Dissolution of the sample in stabilized TCB was carried out by heating at 150-180° C. for about 10 min to 5 hours with occasional, gentle agitation, depending on dissolution temperature and polymer solution. The columns used were, for example, one to three PLgel 20 m Mixed A LS columns (7.5×300 mm) or Waters Styrogel HMW-6E and were calibrated with the integral method using a broad linear polyethylene standard (Chevron Phillips Chemical Company Marlex® BHB 5003 polyethylene) for which the molecular weight distribution had been determined. An IR4 detector (Polymer Char, Spain) was used for the concentration detection.

Example 1

Figure 2:
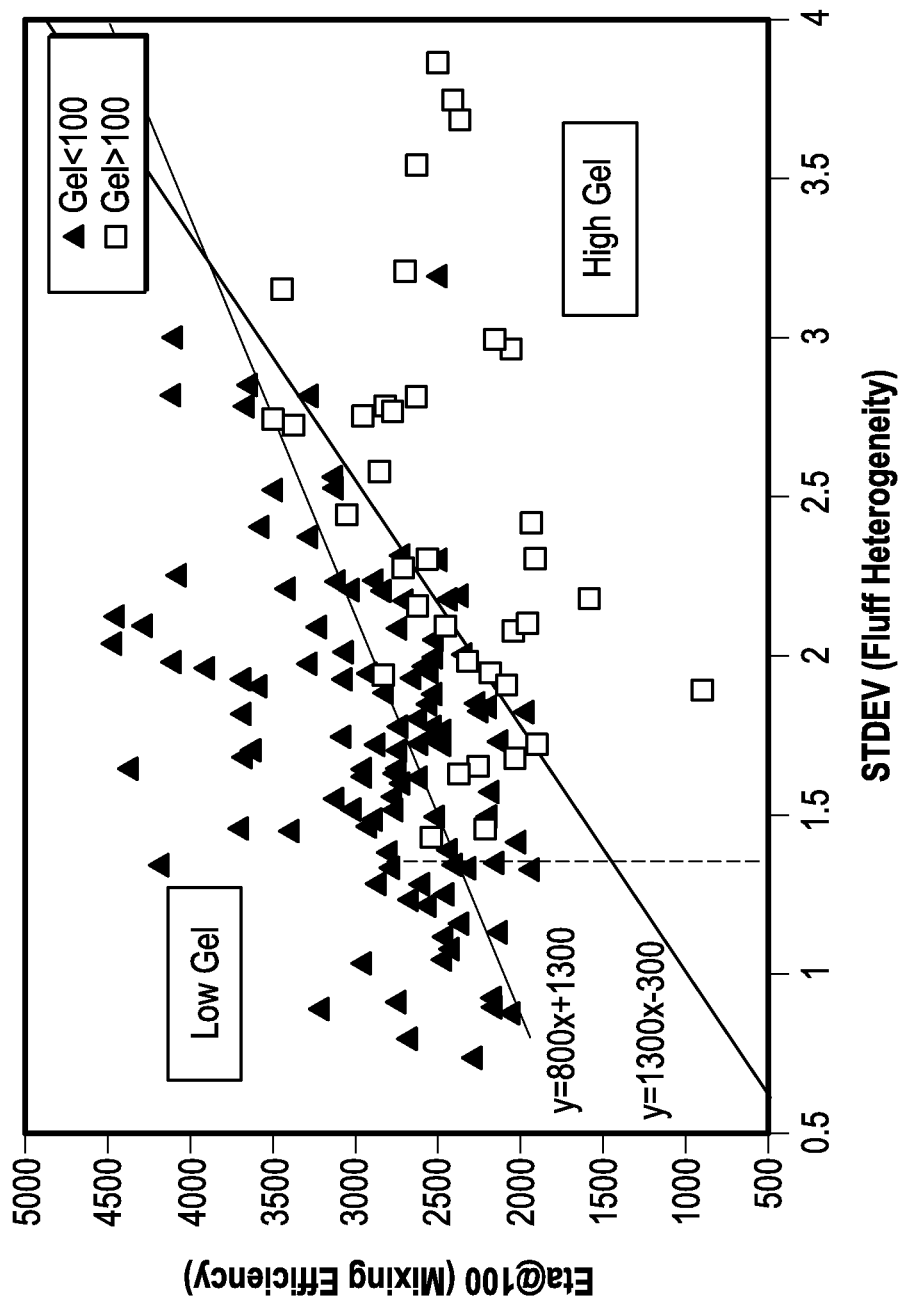
FIG. 2 is a plot of the high frequency viscosity versus the standard deviation $\Omega$ for the samples from example 1.

The disclosed methodologies for estimation of the gel count for a number of polymer compositions were employed. In particular, diversity between the MWD for sieve-separated fluff samples, i.e., compositional diversity, was estimated using the standard deviation $\Omega$, which was determined as the sum of the standard deviations between MWDs for the sieved fluff samples, taken at specific values of the logarithm of molecular weight (Log(M)). The characterization of MWD differences between composite fluff samples focuses primarily on high shear viscosity $\eta@100$. Herein the $\eta@100$ takes its customary meaning as referring to a specific quantitative measure. The resulting plot of $\Omega$ versus $\eta@100$ appears in FIG. 2.

Figure 3:
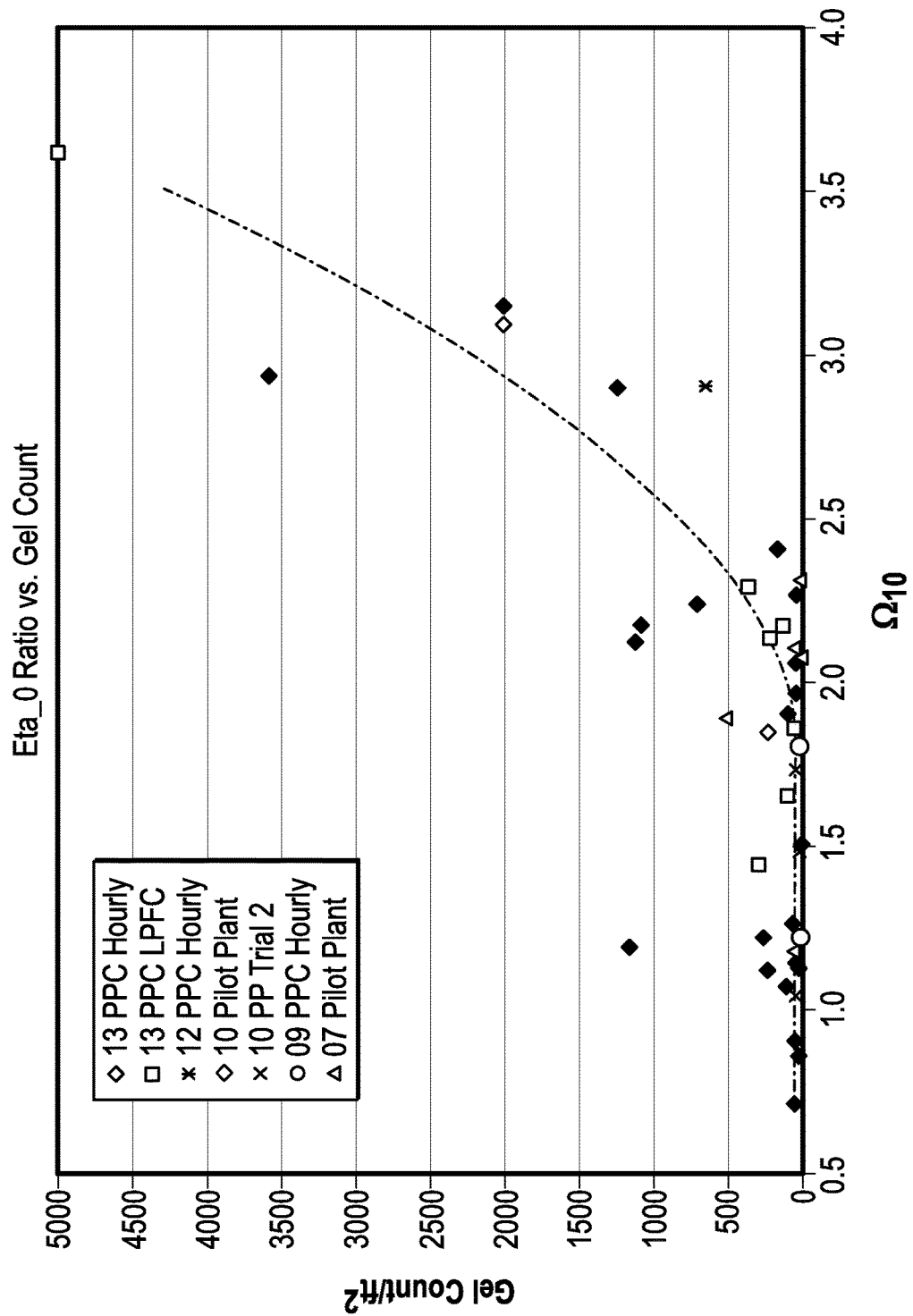
FIG. 3 is a plot of the gel count as a ratio of the zero shear viscosities for the samples from example 1.
Figure 4:
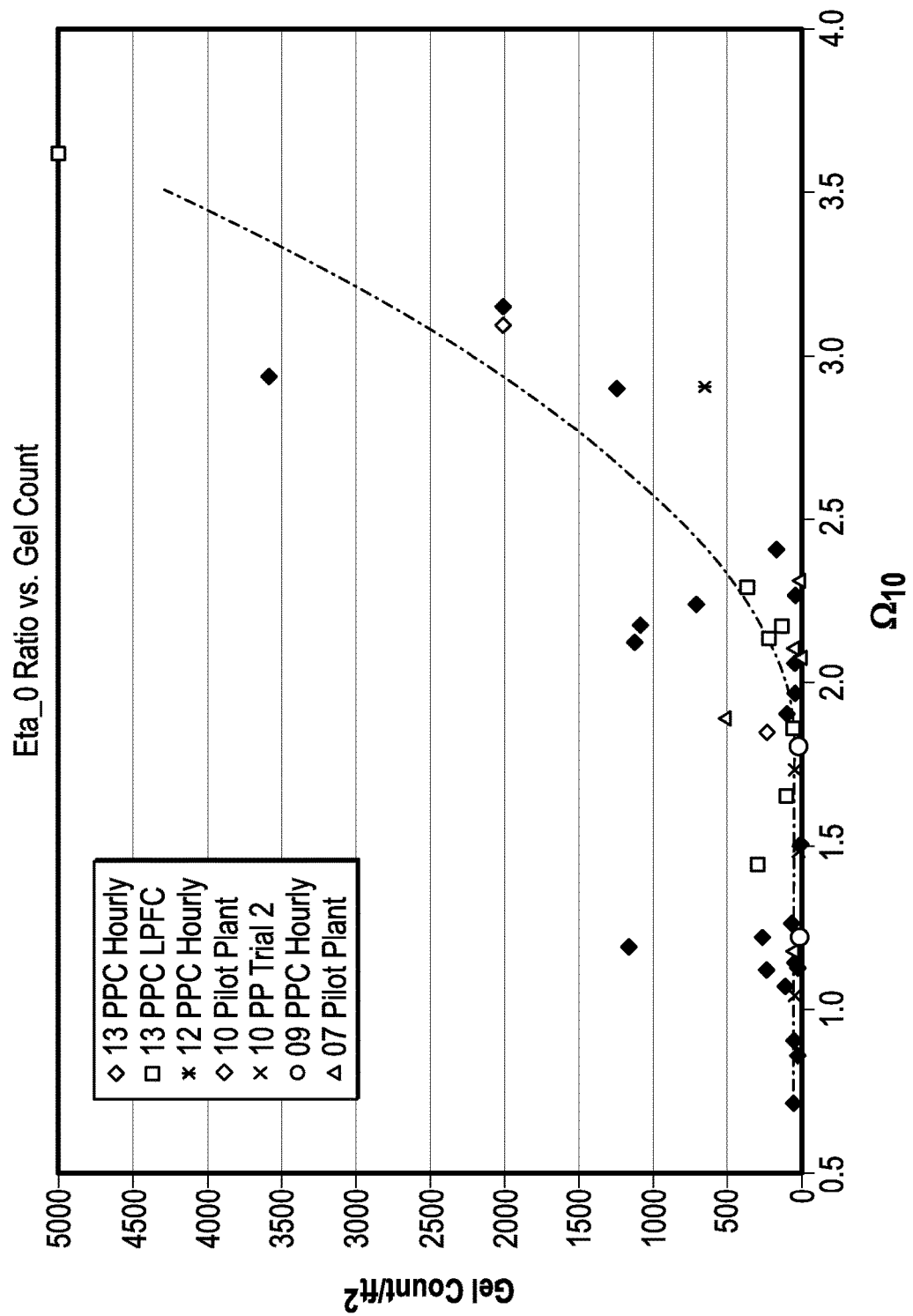
FIG. 4 is a plot of gel count as a function of both the zero shear viscosity and amount of higher molecular weight component for the samples from example 1.

The lines shown on the graph approximately divides the results into 3 groups; specifically, those having low gels (less than about 100 gels/ft$^2$), those having high gels (greater than about 100 gels/ft$^2$), and those where the prediction of gel count is uncertain. For example, those samples expected to produce low gels would have $\theta$ values as determined according to equation 4 of less than 0. In gel, low compositional diversity produces low gel counts. The division line suggests an interaction between diversity and the high frequency viscosity; specifically, the effects of high diversity on gel formation can be overcome by increasing the high frequency viscosity, or equivalently higher mixing efficiency. Mixing efficiency improves with increases in the polymer's high frequency viscosity Without seeking to be restricted by scientific theory, higher viscosity at high shear rate/frequency range could provide better stress transfer during the extrusion process so that better dispersion and lower gels could be achieved. The correlation between gel count and ratio of zero shear viscosity for a sieved sample and that of the composition is shown in FIG. 3 while FIG. 4 illustrates the dependence of gel count on both the amount of HMW component and the zero shear viscosity.

Figure 5:
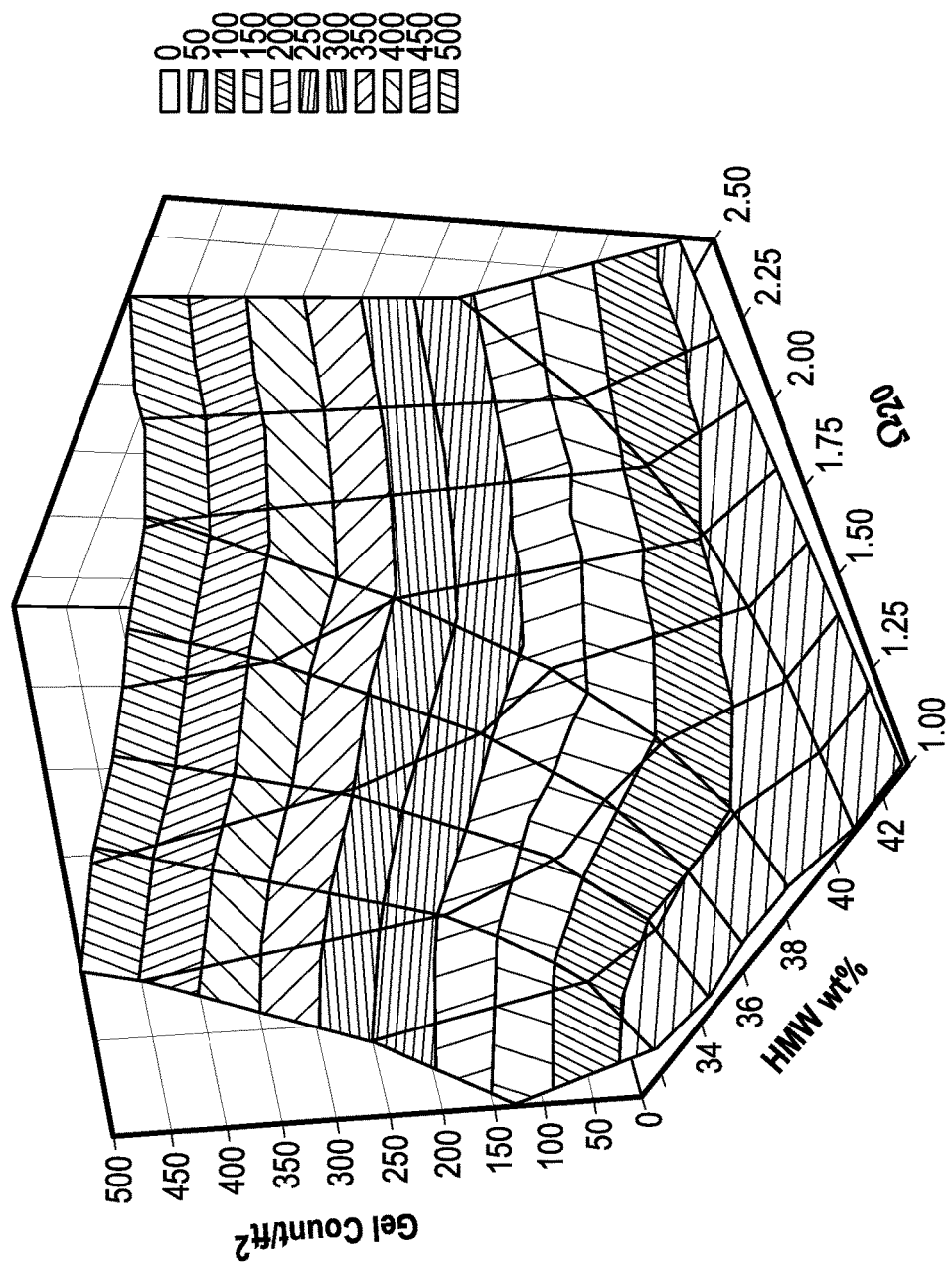
FIG. 5 is a bivariate plot of gel count as a function of $\Omega_{20}$ and the HMW content in the full polymer.

In other words $\Omega_x = \eta_{0\delta x}/\eta_{0\Sigma}$ where $\eta_{0\delta x}$ is the zero-shear viscosity of the x mesh fluff particle while $\eta_{0\Sigma}$ is the zero-shear viscosity of the full polymer. When $\Omega$ was less than 2.0, the majority of samples have low gels. However, when $\Omega$ was greater than 2.0, gels increased rapidly. A closer look at FIG. 3 reveals that there are some samples having high gels, i.e. gels are above the 50 gels/ft$^2$ level when $\eta_{10}$ was less than 2.0. To better correlate gels with fluff attribute, a bivariate distributional plot was used. Shown in FIG. 5 is a bivariate plot of gel count as a function of $\Omega_{20}$ and the HMW content in the full polymer. To do this, the MWD profile of each fluff sample was deconvoluted in order to find out the HMW content (i.e. wt %) using the PeakFit v4.0 software (Jandel Scientific Software, AISN Software Inc.). In the deconvolution process, a chromatography log normal 4-parameter function was used. The HMW content was then rounded up to the nearest integer. Subsequently, the relationship between gel count and compositional diversity, $\Omega_x$, was then established for all samples having the same HMW content. Doing so for all samples of various HMW content resulted in the bivariate distributional plot shown in FIG. 5, wherein the y-axis is the ratio of zero-shear viscosity of the 20 mesh to that of the full polymer, i.e., $\eta_{o\delta 20}/\eta_{o\Sigma}(\Omega_{20})$.

Additional Disclosure

The following enumerated embodiments are provided as non-limiting examples.

A first embodiment which is a method of preparing a polymer article comprising: determining a zero-shear viscosity for a polymer sample sieving the polymer sample to produce a plurality of sieved polymer samples; determining a molecular weight distribution for each of the plurality of sieved polymer samples; determining a zero-shear viscosity for each of the plurality of sieved polymer samples; determining a compositional diversity of each of the plurality of sieved polymer samples based on a ratio of the zero shear viscosity for each of the plurality of sieved polymer samples to the zero shear viscosity for the polymer sample; identifying a polymer sample having a compositional diversity for the polymer sample of less than about 2;
and preparing a polymer article from the identified polymer sample.

A second embodiment which is the method of the first embodiment wherein the polymer sample comprises a higher molecular weight (HMW) component and a lower molecular weight (LMW) component.

A third embodiment which is the method of any the first through second embodiments wherein the HMW component has a weight average molecular weight of from about 300 kg/mol to about 1,000 kg/mol.

A fourth embodiment which is the method of any of the second through third embodiments wherein the LMW component has a weight average molecular weight of from about 10 kg/mol to about 200 kg/mol.

A fifth embodiment which is the method of any of the first through fourth embodiments wherein the sieving is based on a particle size of the polymer sample particles.

A sixth embodiment which is the method of any of the first through fifth embodiments wherein the compositional diversity of at least one of each of the sieved polymer samples has a value of from about 0.85 to about 2.

A seventh embodiment which is the method of any of the first through sixth embodiments wherein the polymer sample comprises polyethylene.

An eighth embodiment which is the method of any of the first through seventh embodiments wherein the polymer sample has a density of from about 0.912 g/cc to about 0.960 g/cc as determined in accordance with ASTM D1505.

A ninth embodiment which is the method of any of the first through eighth embodiments wherein the polymer sample has a melt index of from about 0.01 dg/min to about 1.0 dg/min as determined in accordance with ASTM D1238.

A tenth embodiment which is the method of any of the first through ninth embodiments wherein the polymer sample has a high load melt index of from about 2 g/10 min. to about 30 g/10 min.

An eleventh embodiment which is the method of any of the first through tenth embodiments wherein the HMW component is present in an amount of from about content is from about 35 wt. % to about 65 wt. % based on the total amount of the polymer composition.

A twelfth embodiment which is the method of any of the first through eleventh embodiments wherein a ratio of zero-shear viscosity of the 20 mesh that that of the full polymer, ranges from about 0.8 to about 3.5.

A thirteenth embodiment which is the method of any of the first through twelfth embodiment wherein the polymer article is a film.

A fourteenth embodiment which is the method of any of the first through thirteenth embodiments wherein the polymer article is a pipe.

A fifteenth embodiment which is a method of preparing a polymer article comprising: preparing a polymer sample having a lower molecular weight (LMW) component and a higher molecular weight (HMW) component; sieving the polymer sample to produce a plurality of sieved polymer samples; determining the compositional diversity of each of the plurality of sieved polymer samples based on a molecular weight distribution of each of the plurality of sieved polymer samples; predicting a gel count of an article fabricated from each of the plurality of sieved polymer samples based on the compositional diversity; and fabricating the article from a sieved polymer sample having a predicted gel count of less than about 100 gels/ft$^2$.

A sixteenth embodiment which is the method of the fifteenth embodiment further comprising adjusting one or more parameters of a polymerization reaction for producing the polymer sample subsequent to predicting the gel count wherein adjustment of the polymerization reaction results in a polymer sample having a reduced gel count when compared to the polymer sample prepared without adjustment.

A seventeenth embodiment which is the method of any of the fifteenth through sixteenth embodiments wherein the compositional diversity is further determined by the ratio of the zero shear viscosity for the sieved polymer sample to the zero shear viscosity for the full polymer sample.

An eighteenth embodiment which is the method of any of the fifteenth through seventeenth embodiments wherein the polymer sample comprises polyethylene.

A nineteenth embodiment which is the method of any of the fifteenth through eighteenth embodiments wherein the polymer article is a pipe or a film.

A twentieth embodiment which is a method comprising determining a zero-shear viscosity for a sample of a bimodal polymer; sieving the polymer sample to produce a plurality of sieved polymer samples; determining a molecular weight distribution for each of the plurality of sieved polymer samples; determining a zero-shear viscosity for each of the plurality of sieved polymer samples; determining a compositional diversity of each of the plurality of sieved polymer samples based on a ratio of the zero shear viscosity for each of the plurality of sieved polymer samples to the zero shear viscosity for the polymer sample; and predicting a gel count for an article comprising the bimodal polymer.

A twenty-second embodiment which is a method for predicting gel count in a polymeric article comprising determining a high frequency viscosity of a plurality of polyethylene polymer samples; and identifying a polyethylene polymer composition corresponding to a sample having a high frequency viscosity $\eta@100$ of from about 2000 Pa·s to about 4500 Pa·s, wherein an article fabricated from the identified polymer composition has a gel count of less than about 100 gels/ft$^2$.

A twenty-third embodiment which is a method for predicting gel count in a polymeric article comprising sieving a bimodal polyethylene polymer composition into a plurality of sieved polymer samples; determining a molecular weight distribution for each of the plurality of sieved polymer samples; determining a molecular weight distribution of the bimodal polyethylene polymer composition; determining compositional diversity of the bimodal polyethylene polymer composition according to the equation $\Omega=\Sigma_{n=1}^{74}$ (MWDδ$_x$)$_n$; and identifying a polymer composition having a compositional diversity of from about 0 to about 1.4, wherein an article fabricated from the identified polymer composition has a gel count of less than about 100 gels/ft$^2$.

A twenty-third embodiment which is a method for predicting gel count in a polymeric article comprising (i) for a plurality of bimodal polyethylene polymers having a higher molecular weight (HMW) component and a lower molecular weight (LMW) component, determining one or more parameters selected from the group consisting of a percentage of HMW component; zero shear viscosity; mixing efficiency; compositional diversity; and high frequency viscosity; and (ii) based upon the one or more determined factors, identifying at least one bimodal polyethylene polymer from the plurality, wherein an article fabricated from the identified polymer composition has a gel count of less than about 100 gels/ft$^2$.

A twenty-fourth embodiment which is a method comprising (1) polymerizing olefins to produce a first polymer; (2) predicting a gel count of the first polymer as function of one or more polymer parameters selected from the group consisting of fluff compositional diversity, mixing efficiency, high frequency viscosity η$_{100}$, standard deviation Ω, Eta@100, Eta_0 ratio, and HMW content; (3) adjusting one or more process parameters selected from the group consisting of HMW content, fluff diversity, difference between the weight average molecular weight of the HMW component and the LMW component, and making uniformly active catalytic species on the catalyst; and (4) predicting a gel count of the adjusted polymer as function of one or more polymer parameters selected from the group consisting of fluff compositional diversity, mixing efficiency, high frequency viscosity moo, standard deviation Ω, Eta@100, Eta_0 ratio, and HMW content, wherein the predicted gel count of the adjusted polymer is less than the predicted gel count of the first polymer.

A twenty-fifth embodiment which is the method of the twenty-fourth embodiment wherein the predicted gel count of the adjusted polymer is less than about 100 gels/ft$^2$.

A twenty-sixth embodiment which is the method of any of the twenty-fourth through twenty-fifth embodiments wherein adjusting the one or more process parameters alters a value of fluff compositional diversity, mixing efficiency, 1$^{st}$ moment of HWM area, ΣwR$^2$, Eta@100, Eta_0 ratio, and HMW content of the adjusted polymer in comparison to a value of the same parameter for the first polymer.

Without further elaboration, it is believed that one skilled in the art can, using the description herein, utilize the present disclosure to its fullest extent. While aspects of the disclosure have been shown and described, modifications thereof can be made by one skilled in the art without departing from the spirit and teachings of the embodiments. The aspects and examples described herein are exemplary only, and are not intended to be limiting. Many variations and modifications of the embodiments disclosed herein are possible and are within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an aspect of the present disclosure. Thus, the claims are a further description and are an addition to the detailed description of the present disclosure. The disclosures of all patents, patent applications, and publications cited herein are hereby incorporated by reference, to the extent that they provide exemplary, procedural or other details supplementary to those set forth herein.

What is claimed:

1. A method of preparing a polymer article comprising:
   determining a zero-shear viscosity for a polymer sample;
   sieving the polymer sample to produce a plurality of sieved polymer samples;
   determining a molecular weight distribution for each of the plurality of sieved polymer samples;
   determining a zero-shear viscosity for each of the plurality of sieved polymer samples;
   determining a compositional diversity of each of the plurality of sieved polymer samples based on a ratio of the zero shear viscosity for each of the plurality of sieved polymer samples to the zero shear viscosity for the polymer sample;
   identifying a polymer sample having a compositional diversity for the polymer sample of less than about 2; and
   preparing a polymer article from the identified polymer sample.

2. The method of claim 1 wherein the polymer sample comprises a higher molecular weight (HMW) component and a lower molecular weight (LMW) component.

3. The method of claim 2 wherein the HMW component has a weight average molecular weight of from about 300 kg/mol to about 1,000 kg/mol.

4. The method of claim 2 wherein the LMW component has a weight average molecular weight of from about 10 kg/mol to about 200 kg/mol.

5. The method of claim 1 wherein the sieving is based on a particle size of the polymer sample particles.

6. The method of claim 1 wherein the compositional diversity of at least one of each of the sieved polymer samples has a value of from about 0.85 to about 2.

7. The method of claim 1 wherein the polymer sample comprises polyethylene.

8. The method of claim 1 wherein the polymer sample has a density of from about 0.912 g/cc to about 0.960 g/cc as determined in accordance with ASTM D1505.

9. The method of claim 1 wherein the polymer sample has a melt index of from about 0.01 dg/min to about 1.0 dg/min as determined in accordance with ASTM D1238.

10. The method of claim 1 wherein the polymer sample has a high load melt index of from about 2 g/10 min. to about 30 g/10 min.

11. The method of claim 2 wherein the HMW component is present in an amount of from about 30 wt. % to about 70 wt. % based on the total amount of the polymer sample.

12. The method of claim 1 wherein a ratio of zero-shear viscosity of the identified polymer sample to the zero-shear viscosity of the polymer sample ranges from about 0.8 to about 3.5.

13. The method of claim 1 wherein the polymer article is a film.

14. The method of claim 1 wherein the polymer article is a pipe.

15. A method of preparing a polymer article comprising:
preparing a polymer sample having a lower molecular weight (LMW) component and a higher molecular weight (HMW) component;
sieving the polymer sample to produce a plurality of sieved polymer samples;
determining the compositional diversity of each of the plurality of sieved polymer samples based on a molecular weight distribution of each of the plurality of sieved polymer samples;
predicting a gel count of an article fabricated from each of the plurality of sieved polymer samples based on the compositional diversity; and
fabricating the article from a sieved polymer sample having a predicted gel count of less than about 100 gels/ft$^2$.

16. The method of claim 15 further comprising adjusting one or more parameters of a polymerization reaction for producing the polymer sample subsequent to predicting the gel count wherein adjustment of the polymerization reaction results in a polymer sample having a reduced gel count when compared to the polymer sample prepared without adjustment.

17. The method of claim 15 wherein the compositional diversity is further determined by the ratio of the zero shear viscosity for each of the plurality of sieved polymer samples to the zero shear viscosity for the polymer sample.

18. The method of claim 15 wherein the polymer sample comprises polyethylene.

19. The method of claim 15 wherein the polymer article is a pipe or a film.

20. A method comprising:
determining a zero-shear viscosity for a bimodal polymer sample;
sieving the polymer sample to produce a plurality of sieved polymer samples;
determining a molecular weight distribution for each of the plurality of sieved polymer samples;
determining a zero-shear viscosity for each of the plurality of sieved polymer samples;
determining a compositional diversity of each of the plurality of sieved polymer samples based on a ratio of the zero shear viscosity for each of the plurality of sieved polymer samples to the zero shear viscosity for the polymer sample; and
predicting a gel count for an article comprising the bimodal polymer.

* * * * *